Figure 1:
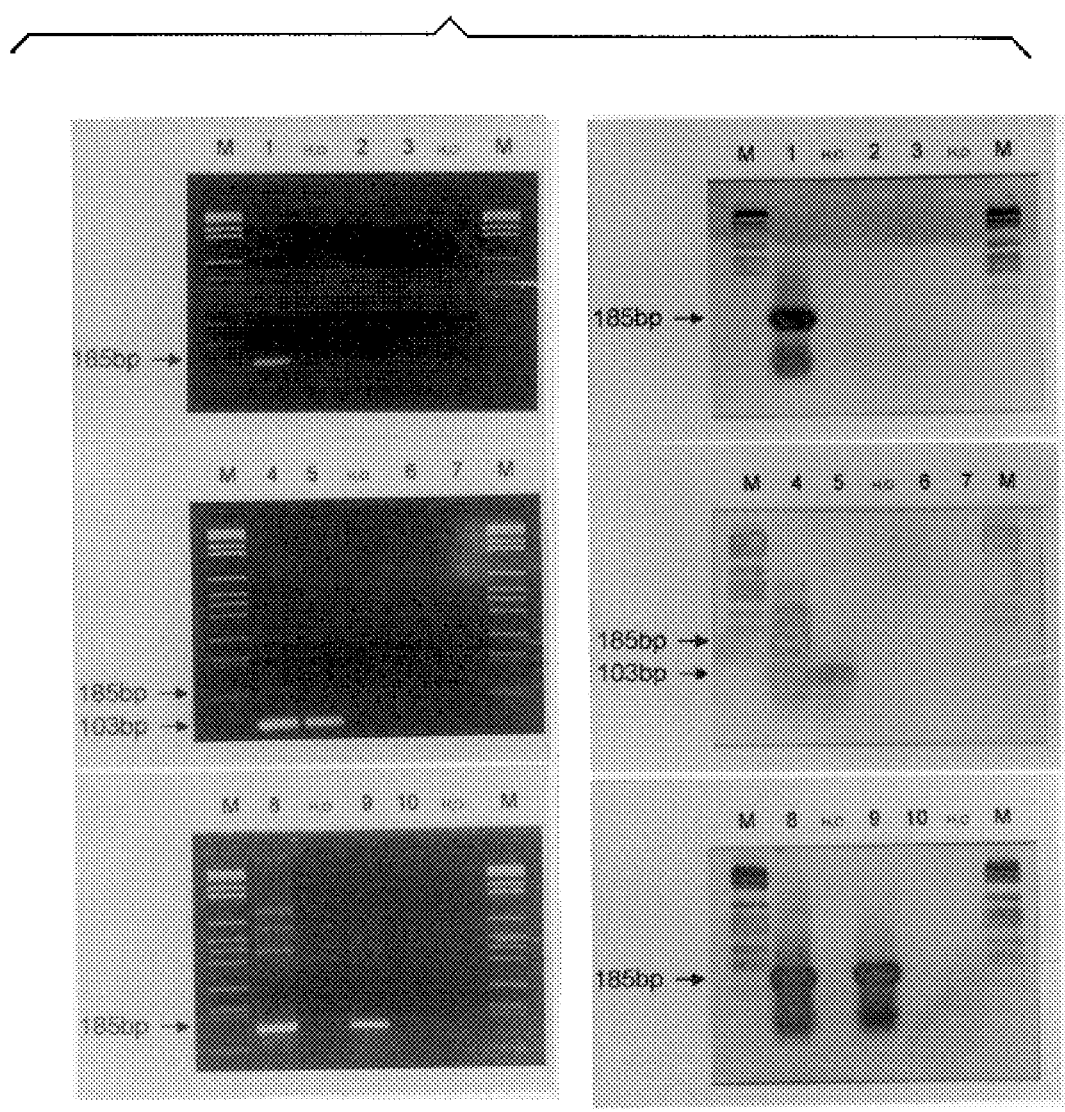

United States Patent

Bauer et al.

[11] Patent Number: 6,124,093
[45] Date of Patent: Sep. 26, 2000

[54] PROCESS FOR REDUCING THE FORMATION OF ARTIFACTS DURING TRANSCRIPTION OF RIBONUCLEIC ACIDS TO DEOXYNUCLEIC ACIDS

[75] Inventors: Peter Bauer; Arndt Rolfs; Vera Regitz-Zagrosek; Eckart Fleck, all of Berlin, Germany

[73] Assignee: Roche Diagnostics GmbH, Mannheim, Germany

[21] Appl. No.: 08/930,601
[22] PCT Filed: Apr. 10, 1996
[86] PCT No.: PCT/EP96/01524
§ 371 Date: Jan. 9, 1998
§ 102(e) Date: Jan. 9, 1998
[87] PCT Pub. No.: WO96/32501
PCT Pub. Date: Oct. 17, 1996

[30] Foreign Application Priority Data

Apr. 11, 1995 [DE] Germany ............................ 195 13 728

[51] Int. Cl.[7] .................................................. C12Q 1/68
[52] U.S. Cl. ............................ 435/6; 435/183; 536/23.1; 536/25.3; 536/25.4
[58] Field of Search ........................ 435/183; 536/23.1, 536/25.3, 25.4

[56] References Cited

U.S. PATENT DOCUMENTS 5,561,058 10/1996 Gelfland et al. ..................... 435/912
5,843,686 12/1998 Zain et al. ........................... 435/7.23

FOREIGN PATENT DOCUMENTS 0 569 272 11/1993 European Pat. Off. .
0 632 134 1/1995 European Pat. Off. .

OTHER PUBLICATIONS

Myers et al. "Reverse Transcription and DNA Amplification . . ." Biochemistry. vol. 30, No. 31. pp. 7661–7666, Aug. 6, 1991.
A. Rolfs et al., Method for Identification of Amplified PCR Products, "PCR: Clinical Diagnostics and Research".
Biotechniques, vol. 13, No. 5, (1992), "Single–Cell cDNA–PCR: Removal of Contaminating Genomic DNA from Total RNA Using Immobilized Dnase I".
Biotechniques, vol. 9, No. 3, (1996), "Use of Reverse Transcriptase Polymerase Chain Reaction to Monitor Expression of Intronless Genes".
Melgar et al., The Journal of Biological Chemistry, vol. 243, No. 17, "Deoxyribonucleic Acid Nucleases".
Deragon et al., "Nucleic Acids Research", 18 (1990) Oct. 25, No. 20, "Use of y irradiation to eliminate DNA contamination for PCR".

*Primary Examiner*—W. Gary Jones
*Assistant Examiner*—Janell E. Taylor
*Attorney, Agent, or Firm*—Arent Fox Kintner Plotkin Kahn

[57] ABSTRACT

A method of transcribing ribonucleic acids of a sample by treating the sample containing ribonucleic acid with a DNA digesting enzyme in the presence of $Mn^{2+}$ ions followed by transcribing the ribonucleic acids into deoxyribonucleic acids and suitable reagents.

27 Claims, 1 Drawing Sheet

PROCESS FOR REDUCING THE FORMATION OF ARTIFACTS DURING TRANSCRIPTION OF RIBONUCLEIC ACIDS TO DEOXYNUCLEIC ACIDS

Subject matter of the invention is a method of transcribing ribonucleic acids (RNA) of a sample into deoxyribonucleic acids (DNA); further, a method of preparing a multitude of DNA molecules with the aid of RNA molecules, reagents for reducing artifacts and reagent kits for implementing said method.

Methods of analyzing nucleic acids can be based on the analysis of both RNA and DNA. Both variants have their advantages. In methods that are based on the analysis of RNA, the ribonucleic acid is first transcribed into deoxyribonucleic acid, the reason being that deoxyribonucleic acids are more stable. However, ribonucleic acids often provide information which is not available when DNA is used, because genomic DNA contains intron sequences that are lost when the RNA is processed by the organism. Methods that are based on the analysis of DNA can, therefore, yield the same result depending on whether or not the sequence to be analyzed contains introns. In cases where only the RNA is to be detected, contamination by DNA leads to a positive alteration of the results unless certain precautions are taken. One possibility of solving this problem is the use of junction primers. Junction primers are oligonucleotides whose sequence is selected such that the 5'-end thereof is complementary to the sequence of the 5'-end of an exon while the 3'-end contains nucleotides that are complementary to the nucleotides of the 3'-end of the adjacent exon but not to the nucleotides of the 3'-end of the intron located between the two in the genome. In this case, the alteration of the result by contaminating DNA can at least be partly avoided.

However, such a distinction cannot be made between DNA and RNA when analyzing transcripts of an intron-free gene. Moreover, pseudogenes pose the same problem as they are identical in length and therefore cannot be distinguished from RNA transcripts. In such cases, it has proven to be advantageous to treat the mRNA sample with RNase-free DNase prior to the transcription reaction. A method of this kind has been described in BioTechniques 9: 262–268 (1990) and BioTechniques 13: 726–729 (1992).

The evaluation of effective DNA digestion when dealing with gene portions that contain introns requires that a part of the RNA that was treated with DNase but not reversely transcribed be subject to a polymerase chain reaction using a primer set which allows discrimination of PCR products according to size that are a result of the cDNA or the genomic DNA.

DNase I requires divalent metal ions (J. Biol. Chem. 243: 4409–4416 (1968)) as a cofactor. It is known that an optimum $Mg^{2+}$-ion concentration is one which exceeds the $Mn^{2+}$ concentration by one order of magnitude. Moreover, it is also known that an increase in the $Mn^{2+}$ concentration does not inhibit the DNase reaction as is the case with $Mg^{2+}$ or $Ca^{2+}$.

Core of the present invention is the finding that the use of $Mn^{2+}$ ions significantly reduces or even completely eliminates the amount of artifact DNA formed by replicative amplification, e.g. by means of the polymerase chain reaction (PCR). Moreover, DNase digestion with $Mn^{2+}$ ions is considerably more effective than with $Mg^{2+}$.

Subject matter of the present invention is therefore a method of transcribing ribonucleic acids of a sample into deoxyribonucleic acids, comprising the following steps:
a. treating the sample containing ribonucleic acid with a DNA-digesting enzyme, followed by
b. transcribing the ribonucleic acids into deoxyribonucleic acids wherein step a. is carried out in the presence of $Mn^{2+}$ ions.

Other subject matters of the invention are a method of preparing a multitude of DNA molecules with the aid of RNA molecules, reagent kits for use in said method, and the use of $Mn^{2+}$ ions to reduce the formation of artifact DNA in transcription reactions.

A ribonucleic acid for use in the present invention can be any desired ribonucleic acid, e.g. mRNA, tRNA, rRNA. The invention works particularly well with mRNA that contains no introns and mRNA that is present as a pseudogene or about which it is not known whether pseudogenes are present or not.

In accordance with the invention, ribonucleic acids can be present even when highly contaminated with corresponding DNA. This is one of the main advantages of the invention. It is therefore possible to use samples containing RNA in the method of the invention which are not completely purified. The content of deoxyribonucleic acids in particular, whether corresponding to the ribonucleic acid used or to foreign deoxyribonucleic acids, can exceed the content in the samples used in accordance with prior art for transcribing the ribonucleic acids. The sample can be taken from any object to be tested, e.g. lysate from tissue or individual cells. The expert is familiar with the preparation of samples that contain ribonucleic acids, especially lysates. The ribonucleic acids can be dissolved in the sample or be immobilized on a solid phase. It is critical for the transcription of the ribonucleic acids that the sample can be reacted with an enzyme that digests DNA.

In a first step, the sample containing ribonucleic acid is treated with a DNA-digesting enzyme in the presence of $Mn^{2+}$ ions. DNA-digesting enzymes are known to the expert. A preferred enzyme is DNase, in particular DNase I. DNase I is an endonuclease that hydrolyzes double-stranded or single-stranded DNA while forming a complex mixture of mono- and oligonucleotides with 5'-phosphorylated ends. Except for the presence of $Mn^{2+}$ ions, the conditions for treating the sample with the solution containing $Mn^{2+}$ ions are not fundamentally different from those applied to the treatment of samples containing ribonucleic acid with DNase solutions containing $Mg^{2+}$ ions. The $Mn^{2+}$ ions present in accordance with the invention are preferably found in a concentration of greater than $10^6$ M. The concentration of $Mg^{2+}$ is preferably between $10^{-5}$ and $10^{-1}$ M, and most preferably between $10^{-4}$ and $10^{-2}$ M. Since the artifact formation associated with DNA may be due to the presence of the $Mg^{2+}$ ions, their use in the digestion solution should be avoided.

To perform the DNA digestion step, a solution is preferably added to the sample to be treated that contains the necessary reagents at a concentration that allows digestion in the resulting reaction mixture. The mixture is then incubated for a sufficient period of time. Preferred incubation periods range between 5 and 60 minutes at temperatures between 36° and 38° C.

The DNA digesting enzyme is then preferably inactivated in a known manner, e.g. by means of heat (5 minutes, 90° C.), or, more preferably, by means of extraction. This is done to avoid redigestion of the deoxyribonucleic acids formed in the subsequent reaction.

The ribonucleic acids are then transcribed into deoxyribonucleic acids. The ribonucleic acids can either remain in the reaction mixture created in the preceding step or purified in an intermediate step. Transcription of the ribonucleic acids can be accomplished in a known manner. To the expert, transcription of ribonucleic acids means the formation of DNA from RNA using RNA as a substrate for the enzymatically catalyzed condensation of monodeoxyribonucleotides. This process is described in Molecular Cloning: A Laboratory Manual, Cold Spring Harbour, N.Y., 1989. A preferred enzyme for the transcription is reverse transcriptase, especially reverse transcriptase from MMLV, particularly superscript (RNase H deleted).

Yet another subject matter of the invention is a method of preparing a multitude of DNA molecules with the aid of RNA molecules, comprising the following steps:
a. treating a sample containing ribonucleic acid with a DNA-digesting enzyme in the presence of $Mn^{2+}$ ions,
b. transcribing ribonucleic acids into deoxyribonucleic acids, and
c. amplifying the deoxyribonucleic acids.

Amplification of deoxyribonucleic acids is understood to be the preparation of a multitude of copies of DNA or parts thereof Methods of amplifying deoxyribonucleic acids are known to the experts. A well-known method of this nature is the polymerase chain reaction (PCR) according to EP-B-0 201 184. In this reaction, a excess amount of primer molecules is added to the deoxyribonucleic acid to be amplified; a part of the primers is complementary to a sequence which does not form the 5'-end while another part of the primer is complementary to the complementary strand; the extension product of each primer is therefore available for extending the other primer. The primers are extended by adding mononucleotide units to the primers in a reaction that is catalyzed by a polymerase.

In accordance with the invention, it is also possible to use junction primers as primers. In a preferred manner, the part which is complementary to the 3'-end of the second exon has a length of 2–4 nt, particularly preferred are 3 nt; the part following in 5'direction of the primer has a length that is sufficient to allow selective hybridization with the 5'-end of the first exon, i.e. 10–30, and most preferably 15–20 nt.

Other methods of amplifying deoxyribonucleic acids are also known, e.g. the ligase chain reaction (LCR) according to EP-A 0 320 308. In this reaction, 2 initial nucleic acids which hybridize on adjacent regions of the DNA are covalently linked. The product of the first two linked nucleic acids serves as a template for linking two additional nucleic acids which hybridize adjacent to the product of the first link. A sequence is amplified in a cyclical reaction.

It is also possible to use the method of WO 90/01069 which comprises both extension and lining reactions for the amplification of deoxyribonucleic acids.

Another possibility of amplifying DNA is the method according to EP A 0 329 822 in which the amplification cycles include a step for the DNA-dependent RNA polymerase reaction.

All of the amplification methods described above generate sequence-specific amplification. Unless complex counter measures are taken and/or particular circumstances are present, these methods would amplify contaminating genomic DNA containing essentially identical sequences as well as deoxyribonucleic acids obtained by transcribing RNA molecules and actually intended for amplification. This, however, usually leads to an undesired background signal that is usually greater than the background signal created by the nucleic acids of other sequences that are normally present in samples containing nucleic acids and which are not to be amplified and/or detected. The invention is therefore particularly well-suited when such methods for the preparation of a multitude of DNA molecules are employed.

Without being bound to this statement, the current results of experiments indicate the following: since no DNA could be detected (e.g. with the PCR using suitable primers) after the sample containing DNA and RNA was treated with the DNA-digesting enzyme, the fact that DNA signals were still present even though the digestion reaction was carried out in the presence of magnesium ions indicates that an artifact construction of the DNA—which is obviously only partially digested—has taken place. When manganese ions are used in accordance with the invention, such a reconstruction obviously cannot occur. This prevents the formation of artifact DNA in the subsequent transcription reaction.

Another subject matter of the invention is a reagent for reducing the formation of artifact DNA during transcription reactions which contains a DNA-digesting enzyme and $Mn^{2+}$ ions. Moreover, this reagent can also contain additional reagents that are commonly necessary to adjust the conditions under which the DNA is digested in samples containing RNA. This includes, in particular, buffers for reaching optimal pH values for the digestion reaction.

Artifact DNA as understood in the invention is DNA which contains genomic sequences but was obtained in an in vitro reaction that was not based on transcription of RNA.

A further subject matter of the invention is a reagent kit for transcribing ribonucleic acids into deoxyribonucleic acids, comprising a DNA-digesting enzyme, $Mn^{2+}$ ions and a reverse transcriptase in separate containers. This kit therefor contains the reagents necessary for steps a. and b. in separate containers. In addition to reverse transcriptase, it is preferable to have $Mg^{2+}$ ions, buffers, the deoxyribonucleoside triphosphates necessary for incorporation and RNase inhibitors for the reverse transcription reaction.

Another subject matter of the invention is a reagent kit for the preparation of a multitude of DNA molecules from RNA molecules, comprising the following in separate containers
a DNA-digesting enzyme and $Mn^{2+}$ ions
a reverse transcriptase, and
reagents for amplifying DNA.

The reagents for amplifying DNA depend upon the amplification method used. The polymerase chain reaction, for example, requires the use of primers specific for the region of the DNA to be amplified, a preferably thermostable, DNA-dependent DNA polymerase and the monodeoxyribonucleoside triphosphates necessary for the desired extension. The necessary reagents are described in EP-B-0 201 184.

The transcripts prepared in accordance with the invention can be used for the detection of RNA originally present in a sample. To accomplish this, the transcription method of the invention is carried out while it can be rendered specific for certain RNA sequences by using sequence-specific primers. The transcript DNA can be amplified if necessary, e.g. in a PCR; the nucleic acids obtained in this manner can then be detected in a known manner; this is accomplished preferably by hybridization on with the nucleic acids probes that are complementary to the nucleic acids followed by detection of the hybridization. The method of the invention is therefore particularly well-suited for the field of nucleic acid diagnostics in molecular biology and clinical laboratory diagnostics.

FIG. 1 shows the formation of transcripts under various conditions; one using $Mg^{2+}$ ions, and the other using $Mn^{2+}$ ions in accordance with the in invention.

The following examples explain the invention in greater detail.

EXAMPLE 1

Isolation of RNA

RNA was extracted from deep-frozen human heart tissue. The samples were homogenized, the entire cellular RNA was extracted with guanidinium thiocyanate/phenol/chloroform (Anal. Biochem. 162:156–15 (1987)) and precipitated at 20,000 g, 4° C. using 100% isopropanol. The pellets were washed with 75% ethanol, dried, and resuspended in DEPC-treated water. All RNA samples were tested by means of PCR to reveal possible DNA contamination (using the pyruvate dehydrogenase gene (PDH)-primer system mentioned below)

DNase I cleavage

1 μg of RNA was treated with 2 U DNase I (Boehringer Mannheim, Germany) for 10 minutes at 37° C. in the presence of 40 U RNasin/μg RNA (Promega, Germany). The final concentrations of $Mg^{2+}$ and $Mn^{2+}$ were 1 mM each. After DNase I digestion, one aliquot was heated up to 90° C. for 5 minutes.

Reverse transcription

90% of the RNA sample treated with DNase I was used in th reverse transcription (RT) reaction. The rest was used as a PCR control. Up to 1 μg of RNA treated with DNase I was incubated with 500 ng of random hexane nucleotides for 10 minutes at 70° C. and then stored at 4° C. In order to start the reaction, a mixture of 100 U Superscript MMLV reverse transcriptase (Gibco-BRL, Germany), 3 mM $MgCl_2$, 50 mM Tris-HCL (pH 8.3), 75 nM KCl, 10 mM DTT, 0.5 dNTPs and 40 U RNasin was added. The sample was incubated in this mixture for 50 minutes at 42° C. The mixture was then heated up to 95° C. for 5 minutes.

Amplification of the deoxyribonucleic acids in a polymerase chain reaction and dot-blot reaction An intron-covering primer system for the pyruvate dehydrogenase gene (PDH) with the plus primer:

5'-GGTATGGATGAGGACCTGGA-3' [SEQ ID NO: 1]

and the minus primer:

5'-CTTCCACAGCCCTCGACTAA-3' [SEQ ID NO: 2]

was used to generate an amplicon of 185 base pairs (bp) in length on the DNA level and 103 base pairs on the cDNA level. Earlier experiments showed that there were no pseudogenes for this PDH gene region. In order to generate larger amplicons (538 bp), the following specific primers plus primer:

5'-CCTTCGACGCACAATGCTTG-3', [SEQ ID NO: 3]

minus primer:

5'-ATGATTGTCCCAAAGCTGGA-3' [SEQ ID NO: 4]

were used for the intron-free angiotensin II-Type I-receptor gene (ATR 1).

The reactions were carried out with 8 pMol of each primer, 50 mMKCl, 10 mM TrisxHCl (pH 8.3), 1.5 mM $MgCl_2$, 100 μM deoxyribonucleoside triphosphates, 0.4 μM of each oligonucleotide, 1.0 U Taq polymerase (Perkin Elmer Cetus) and 50 ng sample nucleic acid in a volume of 25 μl. The reaction was carried out in a 9600™ Perkin Elmer thermal cycler. First, the sample was denatured at 95° C. Then, the following temperature profile was carried out in 40 cycles: 45 sec. 95° C., 60 sec. 60° C., 45 sec. 72° C., followed by 5 minutes at 72° C.

6 μl of the reaction mixture were analyzed in a 3% agarose gel (3% 3:1 NuSieve™, FMC) and subjected to electrophoresis. The gel was then treated with denaturing buffer (1.5 M sodium chloride, 0.5 M sodium hydroxide, for 10 minutes), neutralized for 10 minutes (pH 5.0) and blotted onto a nylon membrane (positively charged nylon membrane, Boehringer Mannheim GmbH). The neutralizing and blotting buffers consisted of 1.0 M TrisHCl 2.0 M NaCl (pH 5.0). The membranes were prehybridized for 30 minutes in 5xSSC-hybridization buffer (1xSSC:0.12 M NaCl, 0.015 sodium citrate, 2.0 w/w per cent of blocking reagent (Boehringer Mannheim GmbH), 0.02 w/w per cent SDS, 0.1 w/w per cent N-lauryl sarcosine). After blotting for 6 hours, the membranes were UV cross-linked with 120 mj (Stratalinker™, Stratagene). Hybridization was carried out for at least 6 hours at 62° C. in 5 ml hybridization solution (containing 2 μl of labeled probes (PCR: Clinical Diagnostics and Research, published by Springer Verlag, Berlin, p. 121 and manufacturer's data) which were synthesized via PCR, denatured in advance with DIG-11-dUTP (Boehringer Mannheim GmbH, Cat. No. 1093657)) in 5xSSC; 0.1% (v/v) N-lauryl sarcosine (Na salt); 0.02%. (w/v) sodium dodecyl sulfate; 2% (w/v) blocking reagent (Boehringer Mannheim, Cat. No. 1096176, casein fraction fat-free dried milk).

The probes were obtained as follows:

When primer pairs were used in the amplified region (plus primer: 5'-TGCTTGGAGAAGAAGTTGCC-3', [SEQ ID NO:5] minus primer: 5'-TCTGGGGGTAACAGTGACCT-3'[SEQ ID NO: 6]), a 94 bp amplicon was directly amplified by the control DNA. This short amplicon was assayed in a preparative 1% NuSieve GTG agarose gel using the ethidium bromide method. The electrophoresis buffer consisted of 0.04 M Tris acetate (pH 8.0). The amplicon was cut out of the gel and 5 ml of the melted agarose were reamplified using the primers listed above and a dNTP label mix with 35% of the dTTP replaced by DIG-dUTP. This probe was used in the hybridization step without further purification.

After washing twice (5 minutes, room temperature) in 2xSSC-0.1% SDS and washing twice again (15 minutes, 62° C.) in 0.2xSSC-0.1% SDS, the membranes were transferred directly into the chromogenic detection buffer (0.1 mol/l maleic acid, 0.15 mol/l sodium chloride, pH 7.5, 0.3 w/w per cent Tween-20).

Chromogen detection was carried out according to Rolfs et al., PCR Clinical Diagnostics and Research, published by Springer Verlag, 1992. In this detection procedure, the membrane was washed with wash buffer for 1 to 5 minutes at room temperature using washing buffer and then incubated in buffer 2 for 30 minutes. The membrane was then incubated for 30 minutes in antibody conjugate solution. The mixture was then washed twice for 15 minutes with 100 ml washing buffer. Then, the membranes were treated for 2 to 5 minutes in buffer 3. The membranes were then incubated in the dark for 6 hours in a solution of 55 μl NBT and 35 ml BCIP in 10 ml buffer 3. The color reaction was stopped for 5 minutes using buffer 4. The color formation was then detected.

The reagents for the chromogen detection were taken from the DIG-DNA Labelling and Detection Kit non-radioactive (Boehringer Mannheim, Cat. No. 1093657) and modified as follows:

Washing buffer:

Buffer: 1+0.3% (w/v) Tween™ 20

Buffer 2: blocking solution 1:10 diluted in buffer 1 (final concentration 1% blocking reagent)

Buffer 3: 0.1 M Tris HCl; 0.1 M NaCl; 50 mM $MgCl_2$; pH 9.5 (20° C.)

Buffer 4: 10 mM Tris-HCl; 1 mM EDTA; pH 8 (20° C.)

NBT: 75 mg/ml in 70% dimethyl formamide (v/v)

BCIP: 50 mg/ml in dimethyl formamide

Result

Although the RNA probes were extracted at least twice with guanidinium thiocyanate/phenol/chloroform, more or less intensive PDH-specific signals showed up in PCR tests, clearly indicating the presence of contaminated DNA, when no further DNase I treatment was carried out (FIG. 1, column 1). After treating a part of the RNA with DNase I with either $Mg^{2+}$ or $Mn^{2+}$ buffer, no other DNA signal (185 bp fragment) was found in the PCR (FIG. 1, columns 2 and 3). When a reaction mixture digested with DNase I/$Mg^{2+}$ buffer was used for the reverse transcriptase reaction, followed by PCR amplification, the specific 103 bp cDNA fragment showed up; surprisingly, however, the 185 bp amplicon of the artifact DNA appeared as well (FIG. 1, column 4). In contrast, only the 103 bp cDNA amp icon became visible when DNAse digestion was performed $Mn^{2+}$ buffer, followed by reverse transcriptase and the PCR (FIG. 1, column 5). The high cleavage efficiency with $Mn^{2+}$ as a cofactor for DNase I is also present when 50 ng of DNA are used with a reaction time of 10 minutes: When both sample are amplified in a PCR reaction (without reverse transcriptase reaction), only the DNase/$Mg^{2+}$ buffer generates an amplicon (FIG. 1, column 9) while the DNaseI $Mn^{2+}$-treated DNA was completely digested (FIG. 1, column 10).

When RNA was assayed for the presence of the 538 bp intron-free AT1R fragment and this reaction mixture was assayed with different amounts of DNase I for different digestion periods (10 minutes, 20 minutes, 30 minutes, 37° C.) it became clear that the greater the quantity of DNase I used and the longer the incubation time, the weaker the AT1R-specific signal became after reverse transcription and PCR, although the specific internal control signals for the short 103 bp PDH fragments were found at the same intensity.

In order to demonstrate whether the DNA signal generated in the reverse transcriptase/PCR reaction after DNaseI/$Mg^{2+}$-treatment was due to the enzymatic properties of the MMLV reverse transcriptase or the Taq polymerase, all experiments were repeated, but without the MMLV enzyme in the reverse transcriptase step. An additional fragment of the size of the DNA in the (pseudo) reverse transcriptase/PCR did not become visible under these conditions when tie DNase I digestion was carried out in the presence of $Mg^{2+}$ ions.

These experiments show that signal differentiation after the reverse transcriptase reaction and PCR was only possible when $MN^{2+}$ as used as a cofactor in order to see whether the signal (generated from RNA by reverse transcriptase reaction) was caused by cDNA or artifact DNA. It is difficult and/or impossible to make a quantitative statement about the number of mRNA copies of a given transcript with buffers containing $Mg^{2+}$. Moreover, transcripts of rare mRNA can be affected by intron-containing genes and therefore provide false-negative results. On the other hand, when dealing with intron-free genes, reassociated DNA fragments generate false-positive signals for mRNA copies that were not transcribed at all.

What is claimed is:

1. A method of transcribing ribonucleic acids contained in a sample into deoxyribonucleic acids, comprising:

(a) combining (1) the sample containing the ribonucleic acids, (2) a solution comprising a DNA-digesting enzyme, and (3) $Mn^{2+}$ ions, in a reaction vessel; and (b) thereafter transcribing the ribonucleic acids into deoxyribonucleic acids.

2. The method of claim 1, wherein the ribonucleic acids are mRNAs which contain no introns.

3. The method of claim 1, wherein steps (a) and (b) are carried out in the same reaction vessel.

4. The method of claim 1, further comprising, between steps (a) and (b), a step of purifying the ribonucleic acids.

5. The method of claim 1, wherein the DNA-digesting enzyme is DNAse I.

6. The method of claim 1, wherein the $Mn^{2+}$ ions are present at a concentration of greater than $10^{-6}$ M.

7. The method of claim 1, wherein the $Mn^{2+}$ ions are present at a concentration of between $10^{-5}$ and $10^{-1}$ M.

8. The method of claim 1, wherein the $Mn^{2+}$ ions are present at a concentration of between $10^{-4}$ and $10^{-2}$ M.

9. The method of claim 1, wherein the $Mn^{2+}$ ions are present at a concentration of between 0.01 and 5 mM.

10. The method of claim 1, wherein the ribonucleic acids are transcribed into deoxyribonucleic acids using an enzyme having reverse transcriptase activity.

11. The method of claim 1, wherein no $Mg^{2+}$ ions are present in step (a).

12. The method of claim 1, further comprising, between steps (a) and (b), a step of inactivating the DNA-digesting enzyme.

13. A method of preparing a multitude of deoxyribonucleic acid molecules using ribonucleic acid molecules, comprising:

(a) combining (1) a sample containing ribonucleic acid molecules, (2) a solution comprising a DNA-digesting enzyme, and (3) $Mn^{2+}$ ions, in a reaction vessel;

(b) thereafter transcribing the ribonucleic acid molecules into deoxyribonucleic acid molecules; and (c) thereafter amplifying the deoxyribonucleic acid molecules to prepare a multitude of deoxyribonucleic acid molecules.

14. The method of claim 13, wherein th DNA-digesting enzyme is DNAse I.

15. The method of claim 13, wherein the $Mn^{2+}$ ions are present at a concentration of greater than $10^{-6}$ M.

16. The method of claim 13, wherein the $Mn^{2+}$ ions are present at a concentration of between $10^{-5}$ and $10^{-1}$ M.

17. The method of claim 13, wherein the $Mn^{2+}$ ions are present at a concentration of between $10^{-4}$ and $10^{-2}$ M.

18. The method of claim 13, wherein the $Mn^{2+}$ ions are present at a concentration of between 0.01 and 5 mM.

19. The method of claim 13, wherein the ribonucleic acids are transcribed into deoxyribonucleic acids using an enzyme having reverse transcriptase activity.

20. The method of claim 13, further comprising, between steps (a) and (b), a step of inactivating the DNA-digesting enzyme.

21. The method of claim 13, wherein the deoxyribonucleic acid molecules are amplified in a polymerase chain reaction.

22. A reagent for reducing formation of artifact DNA during transcription reactions, comprising a solution comprising DNAse I and $Mn^{2+}$ ions.

23. A reagent kit for transcribing ribonucleic acids into deoxyribonucleic acids, comprising a first container containing a solution comprising DNAse I and $Mn^{2+}$ ions; and a second container containing a reverse transcriptase.

24. The reagent kit of claim 23, wherein the second container further contains $Mg^{2+}$ ions.

25. A reagent kit for preparing a multitude of deoxyribonucleic acid molecules using ribonucleic acid molecules, comprising a first container containing a solution comprising DNAse I and $Mn^{2+}$ ions; a second container containing a reverse transcriptase; and a third container containing reagents for amplifying deoxyribonucleic acid molecules.

26. The method of claim 1, wherein the DNA-digesting enzyme is an endodeoxyribonuclease.

27. The method of claim 23, wherein the DNA-digesting enzyme is an endodeoxyribonuclease.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligodesoxyribonucleotide"

(iii) HYPOTHETICAL: NO (xi) SEQUENCE DESCRIPTION: SEQ ID NO: 1:

GGTATGGATG AGGACCTGGA      20

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligodesoxyribonucleotide"

(iii) HYPOTHETICAL: NO (xi) SEQUENCE DESCRIPTION: SEQ ID NO: 2:

CTTCCACAGC CCTCGACTAA      20

-continued (2) INFORMATION FOR SEQ ID NO: 3:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligodesoxyribonucleotide"

(iii) HYPOTHETICAL: NO (xi) SEQUENCE DESCRIPTION: SEQ ID NO: 3:

CCTTCGACGC ACAATGCTTG                                        20

(2) INFORMATION FOR SEQ ID NO: 4:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligodesoxyribonucleotide"

(iii) HYPOTHETICAL: NO (xi) SEQUENCE DESCRIPTION: SEQ ID NO: 4:

ATGATTGTCC CAAAGCTGGA                                        20

(2) INFORMATION FOR SEQ ID NO: 5:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligodesoxyribonucleotide"

(iii) HYPOTHETICAL: NO (xi) SEQUENCE DESCRIPTION: SEQ ID NO: 5:

TGCTTGGAGA AGAAGTTGCC                                        20

(2) INFORMATION FOR SEQ ID NO: 6:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligodesoxyribonucleotide"

(iii) HYPOTHETICAL: NO (xi) SEQUENCE DESCRIPTION: SEQ ID NO: 6:

TCTGGGGTA ACAGTGACCT                                         20